(12) United States Patent
Nagni et al.

(10) Patent No.: US 8,920,171 B2
(45) Date of Patent: Dec. 30, 2014

(54) MODULAR FRAMEWORK SUPRASTRUCTURE FOR DENTAL IMPLANTS

(75) Inventors: Giovanni Nagni, Ancona (IT); Felice Enrico Gherlone, Cossombrato (IT)

(73) Assignees: Biosaf In S.R.L., Ancona (AN) (IT); Giovanni Nagni, Ancona (AN) (IT); Felice Enrico Gherlone, Cossombrato (AT) (IT)

( * ) Notice: Subject to any disclaimer, the term of this patent is extended or adjusted under 35 U.S.C. 154(b) by 0 days.

(21) Appl. No.: 13/984,958

(22) PCT Filed: Dec. 12, 2011

(86) PCT No.: PCT/EP2011/072448
§ 371 (c)(1),
(2), (4) Date: Oct. 25, 2013

(87) PCT Pub. No.: WO2012/110137
PCT Pub. Date: Aug. 23, 2012

(65) Prior Publication Data
US 2014/0051034 A1    Feb. 20, 2014

(51) Int. Cl.
*A61C 8/00*     (2006.01)
*A61C 13/275*   (2006.01)
*A61C 13/273*   (2006.01)

(52) U.S. Cl.
CPC ............. *A61C 8/0009* (2013.01); *A61C 13/275* (2013.01); *A61C 8/0013* (2013.01); *A61C 8/0037* (2013.01); *A61C 8/0048* (2013.01); *A61C 8/0054* (2013.01); *A61C 8/0078* (2013.01); *A61C 13/273* (2013.01)

USPC .......................................................... 433/173

(58) Field of Classification Search
USPC ................................................ 433/173, 174
See application file for complete search history.

(56) References Cited

U.S. PATENT DOCUMENTS

| | | | | |
|---|---|---|---|---|
| 5,219,286 | A * | 6/1993 | Hader | 433/172 |
| 6,905,336 | B2 * | 6/2005 | Summers | 433/214 |
| 7,021,934 | B2 * | 4/2006 | Aravena | 433/173 |
| 2004/0078040 | A1 * | 4/2004 | Feijtel | 606/72 |
| 2004/0142300 | A1 * | 7/2004 | Aravena | 433/76 |
| 2007/0281283 | A1 * | 12/2007 | Lundgren | 433/214 |
| 2010/0209874 | A1 * | 8/2010 | Auderset et al. | 433/174 |
| 2011/0129796 | A1 * | 6/2011 | Riggio | 433/171 |
| 2011/0195379 | A1 * | 8/2011 | Allaire | 433/174 |

FOREIGN PATENT DOCUMENTS

| | | |
|---|---|---|
| EP | 0025419 A1 | 3/1981 |
| WO | 2009033297 A1 | 3/2009 |
| WO | 2009149502 A1 | 12/2009 |
| WO | 2010031188 A1 | 3/2010 |

OTHER PUBLICATIONS

International Search Report for corresponding International Application No. PCT/EP2011/072448.

* cited by examiner

*Primary Examiner* — Ralph Lewis
(74) *Attorney, Agent, or Firm* — Egbert Law Offices, PLLC

(57) ABSTRACT

A modular framework suprastructure for dental implants is provided. The apparatus includes a modular series of stumps and rods with horizontal axis, each of them being composed of a tubular bar provided at one end with an ear with a hole, whereas at the other end of the bar, a clip is applied, being provided with circular hole identical to the aforementioned hole, having suitable dimensions to receive one of said stumps.

7 Claims, 5 Drawing Sheets

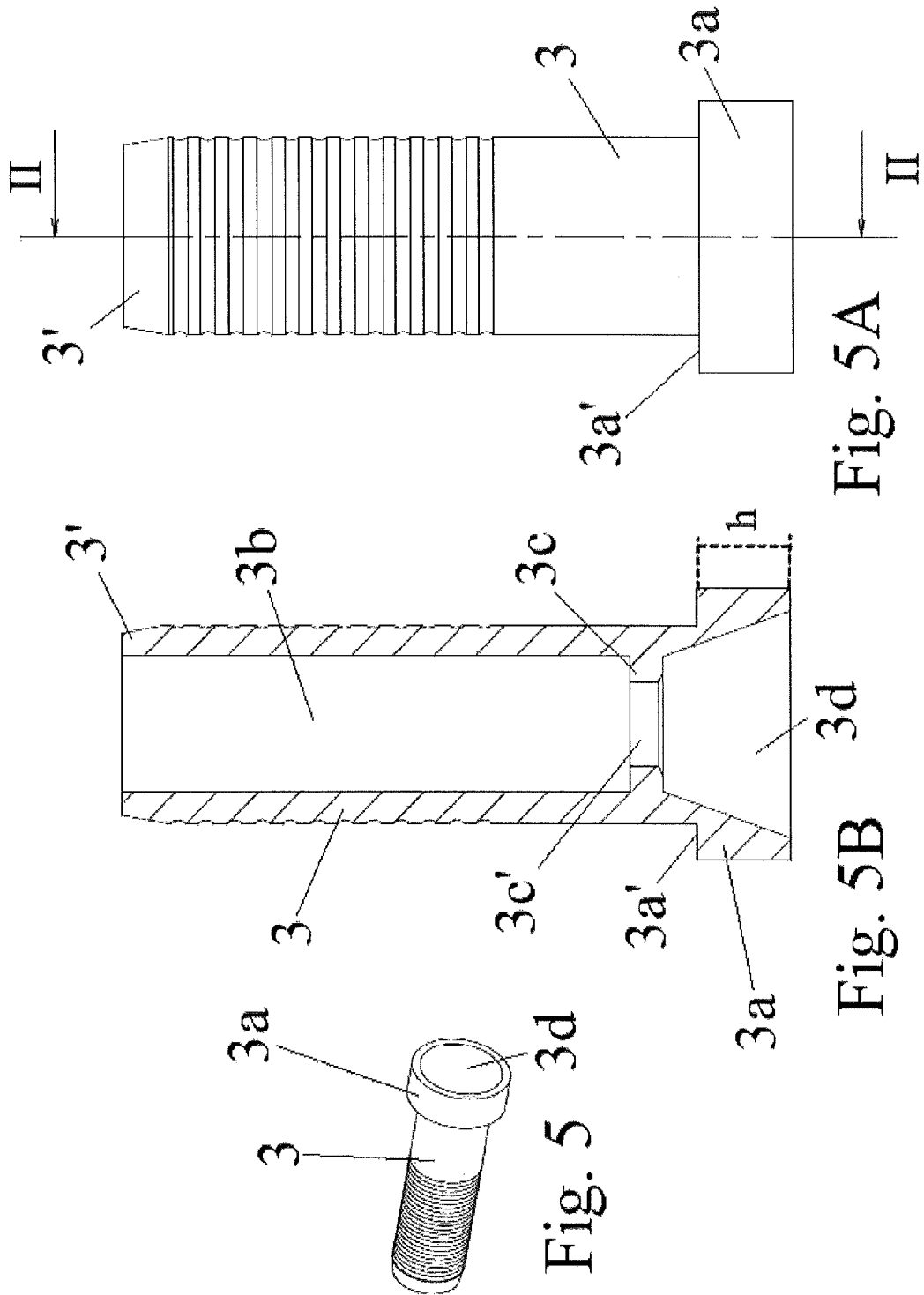

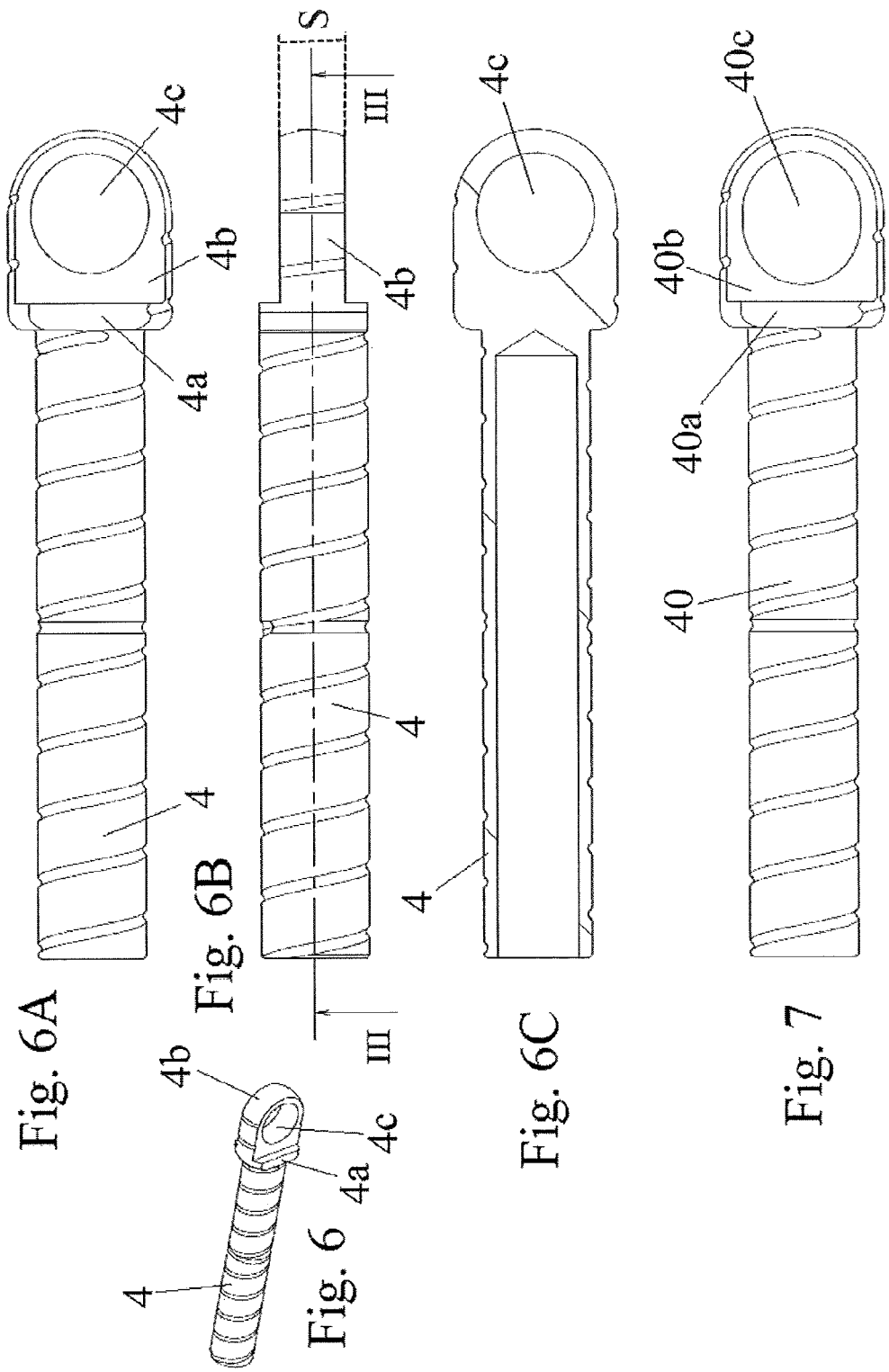

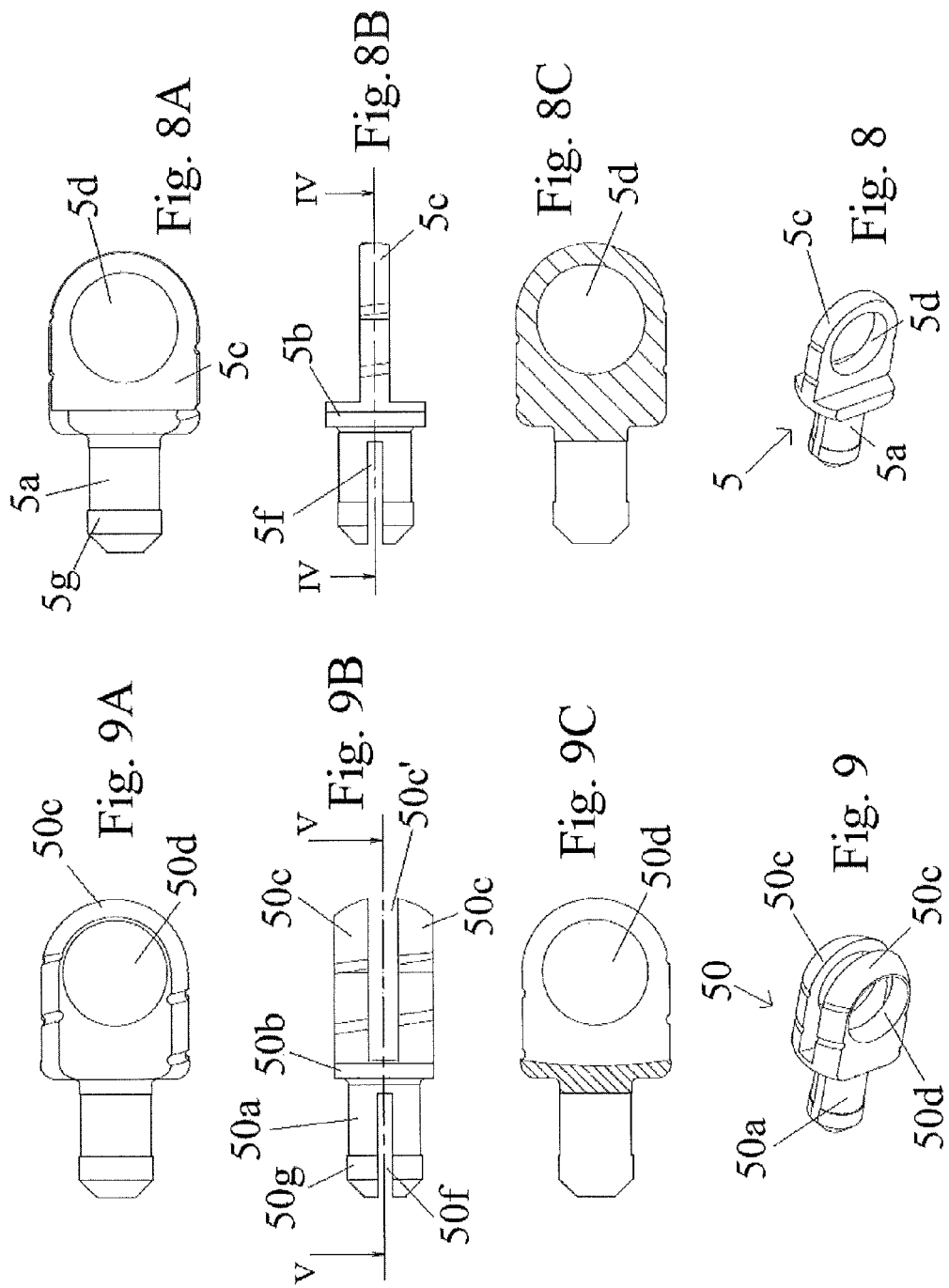

MODULAR FRAMEWORK SUPRASTRUCTURE FOR DENTAL IMPLANTS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present patent application for industrial invention relates to a modular apparatus for prosthezitation and solidarization of dental implants.

2. Description of Related Art Including Information Disclosed Under 37 CFR 1.97 and 37 CFR 1.98

The present patent application for industrial invention relates to a modular apparatus for prosthezitation and solidarization of dental implants.

The peculiarities and advantages of the present invention will be more evident after a brief description of the state-of-the-art.

Firstly, it must be noted that the term "dental prosthesis" refers to a prosthesis for rehabilitation of the masticatory function.

Such a prosthesis is composed of a bearing structure made of acrylic resin on which artificial resin teeth found on the market are mounted; the gingival profile of said prosthesis must have such a configuration to allow for patient's perfect hygiene in the implant area.

In order to fix such a prosthetic structure in the patient's mouth, metal pins with basically cylindrical shape, which are technically defined as "implants", are screwed onto the maxillary or mandibular bone.

Then, a metal stem, which is technically defined as "stump", is screwed onto each of said implants.

In such a context, the stems that protrude vertically from the bone are adapted to create the support structure on which said acrylic resin of the base of the multiple dental prosthesis is incorporated.

Said prosthesis is permanently fixed to said stumps by means of small screws that are engaged from up downwards into the corresponding implants, after passing through small holes obtained in the artificial teeth of said prosthesis.

Once the latter operation is carried out, the small holes obtained on the tip of the prosthesis teeth are cemented.

Based on the above general description, it must be noted that, according to said technology, the implants engaged in the bone must be mutually connected to create a more stable, compact structure, by means of thin metal rods with horizontal direction.

Finally, a further component that is used in such a context is a sort of connection (defined as "sub-stump") positioned between each implant and its corresponding stump.

The use of said connection is necessary when the implant is engaged in the bone in oblique position, which is not compatible with the need to have the stump protrude from the bone in perfectly vertical position.

In such a circumstance the use of said connection is necessary, in view of the fact that said connection is made of two sections with different inclination.

So, the first section is directly engaged into the implant engaged in the bone in sub-vertical position, in such a way that, because of its inclination with respect to the first section, the second section provides from the implant in perfectly vertical position.

Said second section of the connection is now coupled with the lower end of the stump, in perfectly vertical position.

However, it must be noted that, in spite of its large diffusion, the aforementioned technology is impaired by some significant drawbacks.

The first of said drawbacks refers to the difficult installation of said horizontal rods that are used to connect the implants screwed onto the patient's bone; in fact, such a procedure is complicated by the need to operate in correspondence of the maxillary or mandibular bone. A further problem encountered with the traditional technology is the difficulty in ensuring perfect verticality, and consequently perfect parallelism, between the stumps that protrude from the implants that are engaged in the maxillary or mandibular bone.

DE 197 28 268 discloses a modular apparatus for solidarization of dental implants.

WO2010/031188 discloses a modular apparatus for solidarization of denial implants according to the preamble of claim 1.

BRIEF SUMMARY OF THE INVENTION

Based on a similar critical observation of the prior art, the first purpose of the present invention is to allow for easier and quicker solidarization of implants of the prosthesis.

Such a result is obtained by discarding the traditional idea of directly connecting the implants, realizing instead such a connection at the height of the vertical stumps that protrude from the implants.

Such a solution is especially advantageous since it allows for realizing the desired solidarization of the stumps in the dental laboratory, before they are connected by the dentist to the corresponding implants that are already engaged in the patient's bone.

According to the prior art, instead, solidarization of implants at bone level had to be necessarily made in the patient's mouth by the dentist.

Moreover, within the scope of the present invention, a similar connection between stumps is made by means of special bars adapted to operate in horizontal position, which, in addition to be easy to install, are also capable of providing efficacious solidarization between stumps in a perfectly balanced way, thus preventing the onset of undesired "clearance" between stumps and implants, due to possible asymmetric stress produced during mastication.

A further purpose of the present invention is to allow adjacent stumps for assuming and maintaining a perfectly vertical position that favors a balanced, homogeneous transmission of said stress to implants.

In particular, such a result is obtained indirectly, since the apparatus of the invention directly guarantees that the connection bars between stumps have a perfectly horizontal position.

However, considering that said bars are adapted to assume a perfectly perpendicular position to the stumps to be connected, it appears evident that the perfectly horizontal position of said connection bars must necessarily correspond to a perfectly vertical position of the corresponding stumps.

BRIEF DESCRIPTION OF THE DRAWINGS

For purposes of clarity the description of the invention continues with reference to the enclosed drawings, which are intended for purposes of illustration only and not in a limiting sense, wherein:

FIGS. 5, 5A and 5B are respectively an axonometric view, a side view and a sectional view (with plane II-II of FIG. 5A) of the stump of the apparatus according to the invention;

FIGS. 6, 6A, 6B and 6C are respectively an axonometric view, a side flat view, a side cutaway view and a sectional view (with plane III-III of FIG. 6B) of a first embodiment of the bar of the apparatus according to the invention;

FIG. 7 is the same as FIG. 5A, except in that it refers to as second embodiment of the aforesaid bar:

FIGS. 8, 8A, 8B and 8C are respectively an axonometric view, as side flat view, a side cutaway view and a sectional view (with plane IV-IV of FIG. 8B) of a first embodiment of the clip adapted to cooperate with said bar;

FIGS. 9, 9A, 9B and 9C are respectively an axonometric view, a side flat view, a side cutaway view and a sectional view (with plane V-V of FIG. 9B) of a second embodiment of the clip adapted to cooperate with said bar.

DETAILED DESCRIPTION OF THE INVENTION

Figure 2:
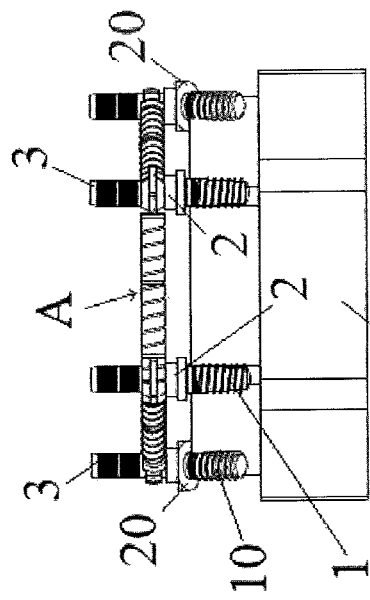
FIGS. 1, 2 and 3 are respectively an axonometric view, a top view and a front view of a metal structure, of which a pan is implanted in the patient's bone and the remaining part is drowned in the dental prosthesis.

Referring to said figures, it must be noted that the components (or modules) of the apparatus of the invention are adapted to cooperate with components (modules) that are traditionally used to compose prostheses of the type screwed onto the patient's bone (OS).

More precisely, said traditional modular components—which are shown in FIGS. 1, 2, 3 and 4—are represented by implants (1, 10) adapted to be screwed onto the bone (OS) and by connection means (2, 20) engaged and fixed on top of said implants (1).

Each implant (1, 10) basically consists in a pointed metal pin with external thread that is axially crossed by a blind cylindrical hole (100).

Each of said connection means (2, 20), which is crossed by an axial cylindrical hole (2a), is composed of as first basically cylindrical section (2b) and a second truncated-conical section (2c) joined by an intermediate flange (2d).

Said cylindrical section (2b) of each connection means (2, 20) is adapted to be exactly inserted and screwed in correspondence of the end of said axial cylindrical hole (100) of the implant (1, 10), whereas the truncated-conical section (2c) is designed to be engaged into the end of a corresponding stump (3).

Still referring to the aforesaid figures, the two central implants (1) are engaged in the bone (OS) in basically vertical position, whereas the two distal implants (10) are engaged in the bone (OS) in inclined position.

Therefore, the two connection means (2) adapted to cooperate with the central implants (1) have a basically rectilinear profile, wherein said cylindrical section (2b) and said truncated-conical section (2c) have coincident axes.

Instead, the two connection means (20) adapted to cooperate with the distal implants (10) have an "angled" profile, wherein the two cylindrical and truncated-conical sections hare intersecting axes.

The use of a similar inclined connection means (20) is necessary to allow the stump (3) for being perfectly vertical, in spite of the fact that the implant (10) is engaged in the bone (OS) with a significant inclination angle.

The modular components of the apparatus of the invention are adapted to cooperate with a structure obtained by assembling said traditional components (1, 10/2, 20).

Referring to FIGS. 5, 5A and 5B, the first component of the new apparatus consists in a stump (3), basically funned of an externally corrugated cylindrical tubular stem with tapered point (3').

The peculiarity of such a stump (3) is that, in correspondence of the end opposite the tapered point (3'), it is provided with enlarged head (3a) that originates a perimeter shoulder (3a').

Such a stump (3) is crossed, for most of its length, by a cylindrical hole (3b) joined, by means of a collar (3c) centrally crossed by a circular hole with lower section (3c'), with a truncated-conical seat (3d) basically obtained at the height of said head (3a).

Figure 4:
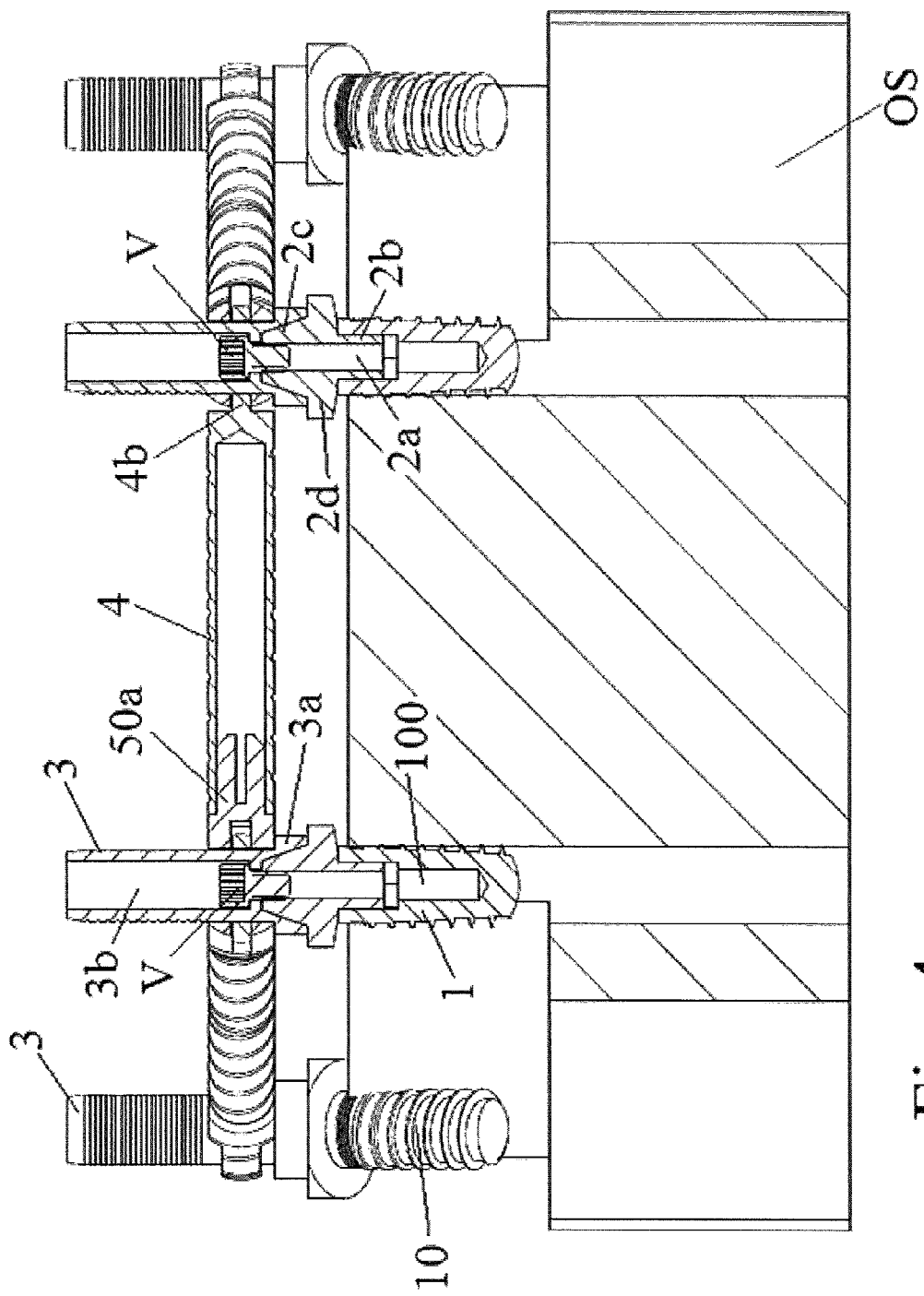
FIG. 4 is a front view of said metal structure, sectioned with plane I-I of FIG. 2.

As shown in FIG. 4, each of said stumps (3) is adapted to be prismatically coupled with one of said connection means (2, 20).

In particular, said coupling provides for the truncated-conical seat (3d) of each stump (3) to be exactly penetrated by the corresponding truncated-conical section (2c) of the connection means (2, 20).

Said coupling can be stabilized by means of suitable fixing screws (V), each of them being adapted to be inserted in the corresponding stump (3) starting from the tapered point of the latter and brought towards the bottom of said cylindrical hole (3b) of the latter, until the enlarged head stops against said internal collar (3c) of the stump (3).

In such to condition, after exactly crossing the hole (3c') provided at the centre of said collar (3c), the stem of the screw (V) is progressively engaged inside said axial hole (2a) of the corresponding connection means (2) in correspondence of the truncated-conical section (2c) of the latter.

The additional components of the apparatus of the invention are used to mutually connect said stumps (3) and consequently also the corresponding implants (1, 10).

Figure 1:
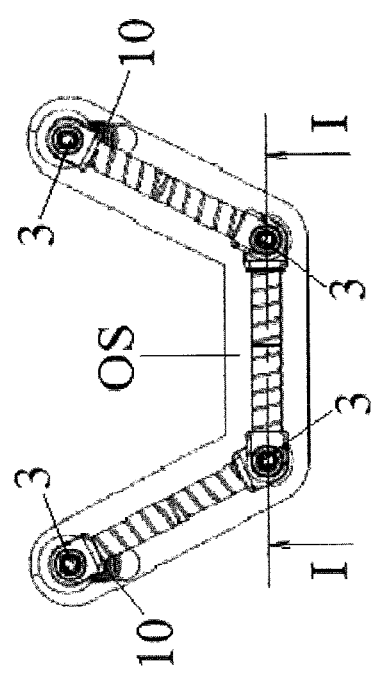
Figure 3:
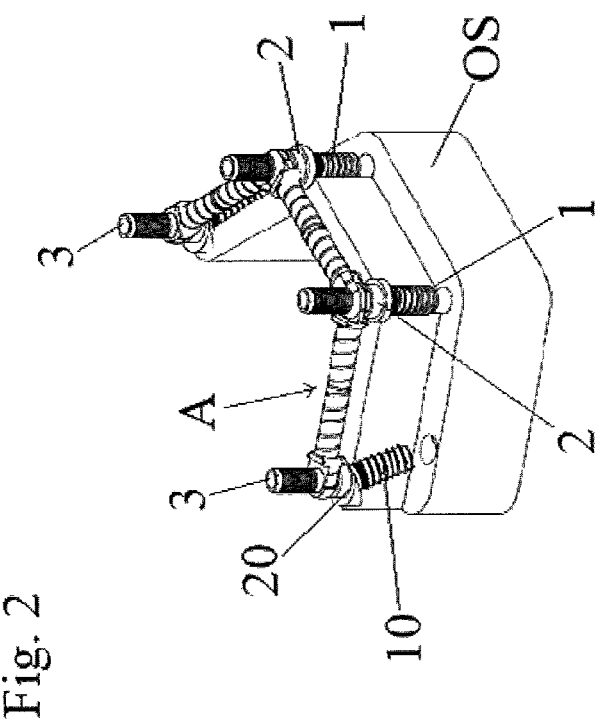

Specifically, the connection between two adjacent stumps (3) is entrusted to a rod with horizontal axis (A), which is expressly shown in FIGS. 1 and 3, obtained from the cooperation of two easy-to-couple modular components (4, 5).

Referring to FIGS. 6, 6A, 6B and 6C, the first of said component consists in an externally corrugated tubular cylindrical bar (4) that is provided at one end, with interposition of a plate (4a), with ear (4b) having a basically arched profile.

Said ear (4b) is crossed by a circular hole (4c) with axis perpendicular to the axis of said bar (4), provided with basically identical section as said stump (3).

As shown in FIG. 6B, in particular, the thickness (S) of said ear (4b) is significantly lower than the diameter of the corresponding tubular cylindrical bar (4).

Referring to FIGS. 8, 8A, 8B, and 8C, the component adapted to cooperate with a similar bar (4) consists in a clip (5), formed of a short cylindrical stem (5a) that protrudes, with interposition of a plate (5b), on the back of an ear (5c) provided with circular hole (5d); it being provided that said plate (5b) and ear (5c) have exactly the same shape and size as the components (4a, 4b) provided on said bar (4).

Moreover, referring to FIG. 8B, said cylindrical stem (5a) is longitudinally cut by a central notch (5f) that extends from the tapered point almost to the connection point with said plate (5b).

In slightly rearward position with respect to said tapered point, a slightly enlarged perimeter border (5g) is provided, with diameter slightly higher than the internal diameter of said tubular cylindrical bar (4).

Said stem (5a) is adapted to be slightly forced in order to penetrate and remain blocked into the free end of a specimen of said bar (4).

When the tip of said stem (5a) is inserted into the bar (4), because of the interference created between the enlarged border (5g) and the internal walls of the latter, the entire stem (5a) tends to narrow in view of the forced approach of the two longitudinal halves, which is made possible by the presence of said central notch (5f).

Considering that the two halves of said stem (5a) tend to enlarge spontaneously because of their intrinsic elasticity, it is evident that the enlarged border (5g) is basically pushed energetically in permanence against the internal walls of the bar (4).

Obviously, the above prevents the "spontaneous" uncoupling of said two cooperating components (4, 5); in fact, uncoupling may only occur following to a sufficiently energetic traction exerted on said clip (5) in order to win the resistance opposed by said interference between said enlarged border (5g) of the stem (5a) of the clip (5) and the internal walls of the bar (4).

However, it must be noted that said bar (4) is adapted to cooperate, alternatively, also with a second embodiment of said clip (50).

Said second clip (50) is provided with a basically identical structure as the first embodiment (5), as illustrated above, except for it is provided with two identical ears (50c) in perfectly specular position and separated by a space (50c) basically having the same height as the thickness (S) of the individual ear (5c) provided in the first embodiment of said clip (5).

FIGS. 9 and 9B illustrate the second embodiment of the dip (50), also with reference to the fact that said ears (50c) have a total thickness, including the space (50c') that is basically identical to the width of the plate (50b).

Obviously, also the second embodiment of the clip (50) is adapted to be disposed in correspondence of the free end of a corresponding bar (4), as illustrated above for the first embodiment (5), and therefore because of the forced insertion of its end (50a), which is also provided with a central longitudinal notch (50f) and enlarged perimeter border (50g) near the tapered point.

In order to complete the installation of the metal bearing structure of a prosthesis, a first specimen of bar (4) is coupled with the first embodiment (5) of the clip, whereas a second specimen of said bar (4) is coupled with the second embodiment (50) of the clip.

Now one of the ears (4b or 5c) of the first specimen of the bar (4) is inserted in the space (50c') between the two ears (50c) provided in correspondence of one of the ends of the second specimen of the bar (4).

When making such a coupling, the hole (4c or 5d) of the individual ear (4b or 5c) of the first specimen of bar must be perfectly aligned with the holes (50d) obtained in correspondence of the pair of ears (50c) provided in the second specimen of bar.

In view of the above, the clip (5) provided with an individual ear (5c) is defined as "male element" and the clip (50) with the pair of ears (50c) is defined as "female element".

Likewise, the term "male element" is used also to indicate the end of the bar (4) associated with the corresponding ear (4b).

In any case, after realizing the above "concatenation" of two adjacent specimens of the bar (4), the latter are coupled with one of said stumps (3), in such a way that the stump (3) simultaneously penetrates said circular holes of the three aligned ears (4c of 5d/50c).

A similar condition is illustrated in FIGS. 2, 3 and 4, wherein such an installation of the adjacent bars (4) is carried out in correspondence of the two stumps (3) fixed to said central implants (1).

The same figures illustrate that coupling between stumps (3) fixed to said distal implants (10) and the ends of the corresponding bars (4) is obtained in correspondence of the individual ear (4b or 5c) that protrudes from said ends.

In particular, coupling between two adjacent "concatenated" specimens of the bar (4) and stump (3) in intermediate position between them is completed when said "male element" of one of said bars (4)—or better said, one of the two ears (50c)—is exactly stopped against said shoulder (3a') of the head (3a) of the stump (3), as shown in FIG. 4.

Moreover, it must be noted that each of said bars (4) is adapted, before being coupled with the corresponding clip (5, 50), to be cut to size, in such a way that its total length, also including the clip, is exactly equal to the distance between the two adjacent stumps (3) to be connected.

Further clarifications are considered necessary on the specific functionalities of the components of the apparatus according to the invention.

First of all, it must be noted that said stump (3) can be made according to multiple alternative embodiments, which only differ in the height (h) of the enlarged head (3a).

In fact, all specimens of the bar (4) connecting the stumps (3) must be disposed in perfectly horizontal position with total coplanarity.

Implants (1, 10) may protrude differently, even though with minimum differential values, from the bone (OS) where they are implanted.

In such a case, a similar difference in height with respect to the bone (OS) would be consequently reproduced also between the corresponding connection means (2, 20) and stumps (3) fixed to said implants (1, 10).

So, obviously, if the heads (3a) of the stumps (3) are disposed at different heights, the adjacent bars—once they are stopped against the heads (3a)—will be disposed in incorrect sub-horizontal position.

The provision of stumps (3) with heads (3a) of different heights (h) allows for efficaciously recuperating said differences in height that may occur between different implants (1, 10).

Obviously, a stump (3) provided with head (3a) with lower height must be mounted on the implant (1, 10) that protrudes the most from the bone (OS), whereas a stump (3) provided with head with higher height must be mounted on the implant (1, 10) that protrudes the least from the bone (OS).

The purpose of the above is to dispose on the same "ideal" horizontal plane the shoulders (3a') of the heads (3a) of the stumps (3), against which said ends of the "concatenated" bars (4) must be positioned.

Likewise, it is necessary to clarify the importance of the fact that the female element of a first specimen of bar (4) and the male element of a second specimen of bar (4) are "coupled" on the same stump (3).

Considering that the bars (4) must have exactly the same length as the distance between the stumps (3), it appears evident that each stump (3) may be subject, possibly because of the stress caused by the normal use of the prosthesis, to simultaneous traction from opposite sides, respectively exerted by the female element of a bar (4) and the male element of the other bar.

The above demonstrates that the traction of the female element of the first specimen of the bar (4) is generated in correspondence of the two circumferential sections of the stump (3) and the traction of the male element of the second specimen of the bar (4) is generated in correspondence of only one circumferential section of said stump (3), included between the two sections affected by the interference of said female element.

The purpose of such a situation is to balance the forces exerted from opposite sides on the stump (3), preventing it from being subject to anomalous, unbalanced bending stress that would be created should two male elements of two adjacent bars (4) be inserted in the stump (3).

Moreover, attention is drawn on FIG. 7, which shows an alternative embodiment (40) of the bar illustrated in FIG. 6A.

The peculiarity of the second embodiment of bar (40) is that the ear (40b), which protrudes from a plate (40a), is provided with hole (40c) with slightly elliptical, and therefore not perfectly circular, profile.

Such an embodiment of the bar (40) is advantageously used when the stump (3) in which the ear (40b) is to be inserted has a slight, undesired inclination, with respect to the perfect vertical, following to a similar misalignment of the implant (1, 10).

In such a case, if the ear (40b) had a perfectly circular hole, it would be impossible to complete its travel along the stump (3) until the ideal stop.

The provision of said elliptical hole (40c) allows for achieving the ideal "stop", given the fact that the "looser" profile of the hole (40c) allows for neutralizing the few degrees of undesired inclination of the stump (3).

A further clarification refers to the presence of the external corrugated surface finish on each stump (3) and each bar (4).

Such a condition is provided to allow the resin used for the base of the multiple dental prosthesis for firmly anchoring against the external surface of the two components (3, 4).

Finally, it must be noted that reference has been made so far to the presence of said connection means (2, 20) in intermediate position between implants (1, 10) and stumps (3).

However, it must be noted that, for the implementation of the present inventive idea, the use of said "intermediate" connection means (2, 20) is not binding, meaning that the stumps (3) of the apparatus of the invention are adapted to be coupled directly with the corresponding implants (1, 10).

In fact, the connection means (2, 20) referred to in the present description are only necessary when some of the implants (1, 10) are implanted in the patient's bone (OS) in inclined position, as in the case of the distal implants (10) shown in FIGS. 1 to 4.

In such a case, the use of the angled connection means (20) in correspondence of the "inclined" distal implants (10) requires the use of the "straight" connection means (2) in correspondence of the central implants (1).

Should all implants be engaged in the bone (OS) in perfectly vertical position, the presence of the connection means would be superfluous and therefore—as illustrated above—the stumps (3) could be directly coupled with the corresponding implants (1, 10).

The invention claimed is:

1. A modular apparatus comprising:
a modular component having an implant of a metal pin form, said implant having a blind cylindrical hole;
a stump having a tubular cylindrical stem with an enlarged head defining a shoulder, said stump having a cylindrical hole joined with a seat by a collar, said collar having a circular hole, said seat adapted to be coupled with said implant;
a tubular cylindrical bar having a first free end and a second end;
a first clip comprising:
 a plate;
 a cylindrical stem protruding from said plate and adapted to be firmly inserted into said first free end of said tubular cylindrical bar; and
 a ring disposed on a back of said plate and having a substantially arched external profile defining a circular hole having a cross-section substantially corresponding to a cross-section of said stump, said ring disposed with an axis perpendicular to an axis of said cylindrical stem, said stump having a tapered point having an external diameter decreasing toward said first free end of said stump, said implant being pointed and having an external thread, said tubular cylindrical bar comprising:
 a plate; and
 a ring at said second end of said tubular cylindrical bar, said ring of said tubular cylindrical bar having a substantially arched external profile defining a circular hole having a cross-section substantially identical to the cross-section of said stump, said ring of said tubular cylindrical bar having an axis perpendicular to an axis of said tubular bar; and
a second clip comprising:
 a plate;
 a cylindrical stem protruding from said plate and adapted to be firmly inserted into said first free end of said tubular cylindrical bar; and
 two identical rings disposed on a back of said plate of said second clip, said two identical rings being in perfect specular position and separated by a space, each ring of said second clip having a substantially arched external profile and defining a circular hole having a cross-section substantially identical to a corresponding cross-section of said stump and disposed with an axis substantially perpendicular to an axis of said cylindrical stem of said second clip, the space between said two identical rings of said second clip suitable for receiving said ring of said tubular cylindrical bar or said first clip such that said stump can be received into the holes of the ring of said second clip and into the hole of said ring of said tubular cylindrical bar or said first clip.

2. The modular apparatus of claim 1, further comprising:
an additional modular component having a tubular cylindrical bar with a plate and a ring, said ring of said additional modular component having a substantially arched external profile defining an elliptical hole adapted to be penetrated by said stump and disposed with an axis perpendicular to an axis of said tubular cylindrical bar of said additional modular component.

3. The modular apparatus of claim 1, said ring of said tubular cylindrical bar having a thickness substantially less than a diameter of said tubular cylindrical bar.

4. The modular apparatus of claim 1, said stems of said first and second clips being cut by a longitudinal notch and having an enlarged perimeter border, said enlarged perimeter border having a diameter slightly greater than an internal diameter of said tubular cylindrical bar.

5. The modular apparatus of claim 1, further comprising:
   a connector interposed between said stump and said implant, said connector having a joint having a first generally cylindrical section adapted to be inserted inside of said cylindrical hole of said implant, said connector having a second section adapted to be exactly inserted into said seat of said stump, said first generally cylindrical section and said second section being joined by an intermediate flange.

6. The modular apparatus of claim 1, said tubular cylindrical bar having an external corrugated surface.

7. The modular apparatus of claim 1, said stump having an external corrugated surface.

\* \* \* \* \*